United States Patent [19]
Voigt et al.

[11] 3,976,934
[45] Aug. 24, 1976

[54] METHOD AND APPARATUS FOR THE CONTINUOUS, CONTACTLESS TESTING OF A LONG CONDUCTOR WHICH CONSISTS AT LEAST PARTIALLY OF SUPERCONDUCTIVE MATERIAL

[75] Inventors: Hans Voigt, Erlangen-Kosbach; Günther Rupp, Nunberg, both of Germany

[73] Assignee: Siemens Aktiengesellschaft, Munich, Germany

[22] Filed: June 26, 1975

[21] Appl. No.: 590,678

[30] Foreign Application Priority Data
July 1, 1974 Germany............................ 2431505

[52] U.S. Cl................................ 324/34 SC; 29/593
[51] Int. Cl.²......................................... G01R 33/12
[58] Field of Search................ 324/37, 40, 43 R, 45, 324/34 R, 34 SC; 307/306; 335/216; 29/599, 593; 336/DIG. 1

[56] References Cited
UNITED STATES PATENTS
3,497,844   2/1970   Carruthers et al.................. 335/216

OTHER PUBLICATIONS
F. Wittaenstein et al.; Test Facility for Large Superconducting Strips; Cryogenics; June, 1969, pp. 158–164.

*Primary Examiner*—Robert J. Corcoran
*Attorney, Agent, or Firm*—Kenyon & Kenyon Reilly Carr & Chapin

[57] ABSTRACT

A method and apparatus for the continuous, contactless testing of a long conductor which consists at least partially of superconductive material in which the conductor is moved, with the superconductive material in the superconducting state, through an external magnetic field which induces shielding currents in the superconductive material, while the magnetic field produced by these shielding currents is measured.

10 Claims, 4 Drawing Figures

METHOD AND APPARATUS FOR THE CONTINUOUS, CONTACTLESS TESTING OF A LONG CONDUCTOR WHICH CONSISTS AT LEAST PARTIALLY OF SUPERCONDUCTIVE MATERIAL

BACKGROUND OF THE INVENTION

The invention relates to superconductors in general and more particularly to a method and apparatus for the continuous, contactless testing of a long conductor consisting at least partially of superconductive material.

In the construction of superconducting coils such as magnet coils for generating strong magnetic fields or of superconducting windings for electric machines it is difficult to determine whether the conductor used, which as a rule is a conductor in wire, ribbon, cable or stranded form consisting of superconductive material and electrically normal-conducting metal, meets the specified requirements over its entire length, particularly with respect to its critical current and its magnetic field dependence as well as to other electrical and magnetic variables. Heretofore, sections were usually taken from the ends of the individual lengths of the conductor after manufacture. These were equipped with current leads and voltage probes and tested in an external magnetic field. However, it was still not known to what extent such test results were representative of the entire length of the conductor. Even if further samples are cut from the individual lengths of the conductor manufactured the values measured thereon will not necessarily be representative of the entire conductor length. Such a procedure furthermore has an undesirable consequence in that a length of conductor is cut up into smaller sections. Continuous testing for the respective conductor properties of interest over the entire length of the conductor and finding externally invisible faults, with, for instance, a lower critical current than the remaining conductor parts, have heretofore not been possible. On the other hand superconducting magnet coils particularly, often do not reach the operating performance data which are expected on the basis of measured values obtained from the end sections of the conductor or other samples. For this reason they have usually been relatively heavily overdesigned. Similar problems also arise with long superconducting wires and ribbons which are used in superconducting cables.

SUMMARY OF THE INVENTION

It is an object of the present invention to enable the continuous, contactless testing of any desired length of a conductor which consists at least partially of superconductive material, before the conductor is wound, for instance, into a coil.

According to the present invention this problem is solved by moving the conductor, with the superconductive material in the superconducting state, through an external magnetic field which induces shielding currents in the superconductor material and by measuring the magnetic field generated by these shielding currents.

Among other things the method according to the present invention permits the determination of the location dependence of the critical current, i.e., that current which the superconductor material is just still able to support without going into a normally conducting state, along the length of the conductor. For, this critical current is proportional to the magnetic field produced by the shielding currents. With the method according to the invention defective points, such as breaks or portions damaged due to excessive bending of the conductor which result in a local reduction of the critical current can be ascertained. By means of the method according to the present invention it is also possible to predict the stability behavior of the conductor, i.e., its susceptibility to jumps of the magnetic flux. The method according to the present invention can be used for any long conductors which consist at least partially of superconductive material. However, it is particularly well suited for testing conductors in ribbon form because of the favorability of that geometric configuration.

The method is suitable for testing conductors which have continuous layers of superconductor material, as well as for testing what are known as multi-core conductors. In the latter a large number of filaments or wire superconductor cores are embedded in a normally conducting matrix.

The method according to the present invention can be carried out in a simple manner by passing the conductor to be tested through an external magnetic field which is constant in time. But the conductor can be moved also through an external magnetic field which is variable in time. This latter form of the method has the advantage that the change of the magnetic field in time to which the conductor is subjected can be varied even if the conductor runs through the magnetic field with constant speed. The rate of change of the field and the speed at which the conductor runs through the external magnetic field are thereby decoupled. Such a variation of the field change in time can be of interest particularly if the upper limit of field change frequency at which the conductor to be examined is stable is to be investigated. The stability of the conductor then manifests itself if the magnetic field produced by the shielding currents is independent of the frequency of change of the external magnetic field. In addition, information can be obtained through changing the field independently of the passage velocity of the conductor through the external magnetic field such as information regarding the currents that appear in the normally conducting matrix of a multi-core conductor due to the field change.

It is particularly advantageous to make the change of the external magnetic field acting on the conductor large enough that the induced shielding currents reach the critical current density over the entire cross section of the superconductive material. This is particularly true where the critical current of the conductor or the spatial distribution of the critical current along the conductor, i.e., the homogeneity of the critical current, is to be measured. For, if the critical current density is not reached over the entire cross section of the superconductor material, inhomogeneities in the spatial distribution of the critical current along the conductor may be at most only very faintly noticeable.

For implementing the method according to the present invention, apparatus which comprises a cryostat, a cylindrical superconducting magnet coil arranged in the cryostat for generating the external magnetic field, means for introducing the conductor into the magnetic field of the superconducting magnet coil approximately parallel to the axis of the coil, means for deflecting the conductor perpendicularly to the coil axis and therefore, to the external magnetic field, and, finally, means for bringing the conductor out of the magnetic field again parallel to the coil axis, and in which at least one magnetic field probe is provided in the vicinity of the deflection point has been found particularly advantageous. It is particularly advantageous to provide a magnetic field probe both above and below the conductor in the vicinity of the deflection point. By adding the measured signals of the two probes measurement errors which are caused by changes in the distance between the conductor and the measuring probes during measurement can be compensated in a simple manner. An additional coil may be provided at the deflection point for generating an additional, time-variable external magnetic field directed perpendicular to the conductor.

Hall-effect probes are particularly well suited as magnetic field probes. However, other magnetic field probes, e.g., magnetic-field dependent resistors, known as field plates, as well as small induction coils and suitable superconducting probes (SQUID) can be used.

DETAILED DESCRIPTION OF THE PREFERRED EMBODIMENT

Figure 1:
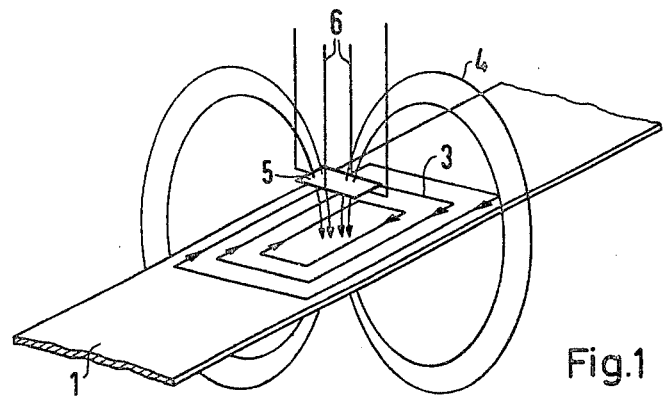
FIG. 1 is a diagram illustrating the measuring principle of the present invention.

FIG. 1 illustrates a conductor 1 which consists at least partialy of superconductive material in the form of a ribbon in the superconducting state exposed to an external magnetic field which is represented by the arrows 2. By superconducting state is meant that the conductor is cooled to the point where its superconductive material will conduct current essentially without loss. The field 2 in the case of the illustrated ribbon shaped conductor is preferably perpendicular to the broad side of the ribbon. When the conductor 1 moves through the external magnetic field 2 shielding currents 3 are induced in the superconductive material of the conductor 1. These in turn generate a magnetic field 4. Above or below the ribbon plane of the conductor 1, magnetic fields 4 off the shielding currents can be measured as an attenuation of the external magnetic field 2 using a magnetic field probe 5, e.g., a Hall probe. In order to measure the magnetic field 4 directly, the measured signal taken off the Hall electrodes 6 of the Hall probe 5 can advantageously be compensated so that the output signal is just zero when no conductor 1 is in the external magnetic field 2. The measured signal which appears when the conductor 1 is introduced into the external magnetic field 2 is then proportional to the magnetic shielding field 4. Furthermore, since the critical current always flows in the superconductive material of the conductor 1 when the latter has been subjected to a sufficiently large change of the external magnetic field 2, the magnetic shielding field 4 is also proportional to the critical current of the conductor 1. For a homogeneous current distribution over the cross section of the conductor 1 the critical current $I_c$ can be determined from the compensated Hall voltage $U_H$ from the following relation:

$$I_c = (U_H \cdot F)/(\alpha H \cdot B_y),$$

where $\alpha_H$ is the sensitivity of the Hall probe, F the cross section of the superconductor material of the conductor and $B_y$, the component of the shielding field normal to the plane of the ribbon, divided by the current density.

For a non-homogeneous current distribution over the superconductor cross section, but the same local current density as for homogeneous current distribution, the shielding field 4 is smaller and depends on the current distribution. The proportionality factor between the critical current and the magnetic shielding field, however, can be calculated in each case or determined by comparison measurements.

The attainable magnetic shielding fields are large enough to be easily measured. In the case of a conductor about 2 mm wide and about 70 μm thick, which has a superconductive Nb₃Sn coating about 9 μm thick at its surface, and in an external magnetic field with a magnetic induction of 2 tesla carries a critical current density of about $10^6$ A/cm², a shielding field of about 0.03 T is measured with a distance of the Hall probe from the ribbon surface of about 0.7 mm. The shielding field is in this case about 1.5% of the external magnetic field. If a Hall probe of about 0.4 mm wide is used, the shielding field is also sufficiently homogeneous over the width of the probe to allow a reliable measurement. A distance of the Hall probe from the ribbon surface of the conductor 1 of about 0.7 mm has been found advantageous since with such a distance from the ribbon surface, the shielding field 4 is large enough to be measured but does not vary as much with the distance from the ribbon surface as it would in the immediate proximity of the ribbon surface. With a distance of 0.7 mm, the measurement is therefore relatively insensitive to small changes in the distance during the measurement. As mentioned above a further Hall probe at about the same distance below the underside of the ribbon of the conductor can advantageously be provided. The measured signals of the two Hall probes are then added to further compensate for distance changes. With such an arangement only one Hall probe measures a higher shielding field when the position of the ribbon-shaped conductor 1 changes, while the other Hall probe moves to a region of the shielding field with a smaller field strength. As a result the sum signal is largely independent of position changes of the conductor 1.

A preferred apparatus for carrying out the method according to the present invention, using the measuring principle explained with reference to FIG. 1 is shown schematically in FIG. 2. A portion of this apparatus is shown in more detail in FIG. 3. The ribbon conductor 12 to be tested runs from a supply reel 11 via a guide pulley 13, for instance, and a polytetrafluoroethylene feedthrough into a cryostat 14 which contains a supply 15 of liquid helium. A cylindrical superconducting magnet coil 16 is arranged in the liquid helium and generates the external magnetic field which acts on the conductor 12. Inside the opening 17 in the coil 16 the magnetic field produced by the coil can reach up to 5 teslas. The conductor 12 is first introduced into the helium bath 15 and cooled down to superconductivity. It is thereupon introduced into the opening 17 in the superconducting magnet coil 16, where it initially runs approximately in the direction of the coil axis, parallel to the external magnetic field. In the zone of maximum field strength of the external magnetic field, the conductor 12 is then deflected by a roller 18 with a diameter of, for instance, about 40 mm in such a way that at the lowest point of the deflection roller the external magnetic field generated by the superconducting magnet coil 16 is normal to the ribbon surface of the conductor 12. Considering the component of the magnetic field normal to the ribbon surface of the conductor 12, it can be seen that the ribbon shaped conductor 12 is subjected to a change of the external magnetic field from about the value zero to the maximum field strength one-quarter of the circumference of the roll 18. Because of this change in the field strength, shielding currents are induced in that part of the conductor 12 which is situated in the vicinity of the deflection point.

Figure 3:
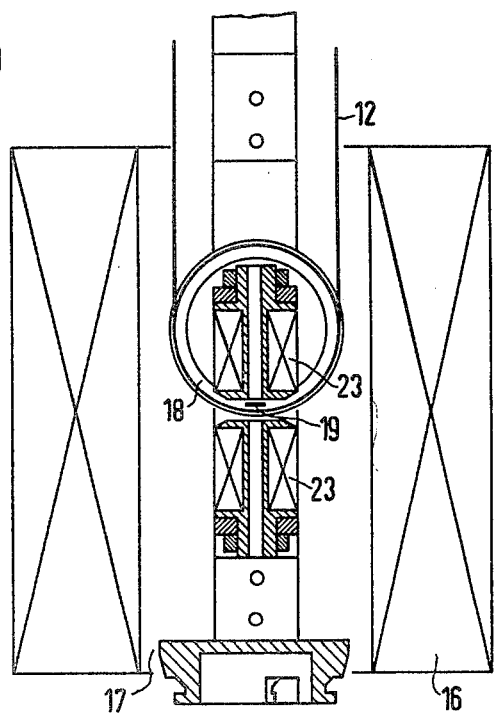
FIG. 3 illustrates a detail of the apparatus according to FIG. 2.

A Hall probe 19 is mounted inside the roller 18. After deflection around the roller 18, the conductor 12 is then brought out again, first out of the magnetic field of the coil 16 in a direction approximately parallel to the axis of the coil and then out of the cryostat 14, and is wound on a reel 21 via a guide pulley 20. The conductor can advantageously be transported by motor driven friction wheels 22 which pull the ribbon shaped conductor 12 through the apparatus. A ribbon velocity of about 100 m/hr has been found feasible. In FIG. 3 a small magnetic double coil 23 which can generate locally limited field changes or an additional magnetic field varying in time, the magnetic field produced also being normal to the ribbon surface of the conductor 12 is also shown.

Figure 2:
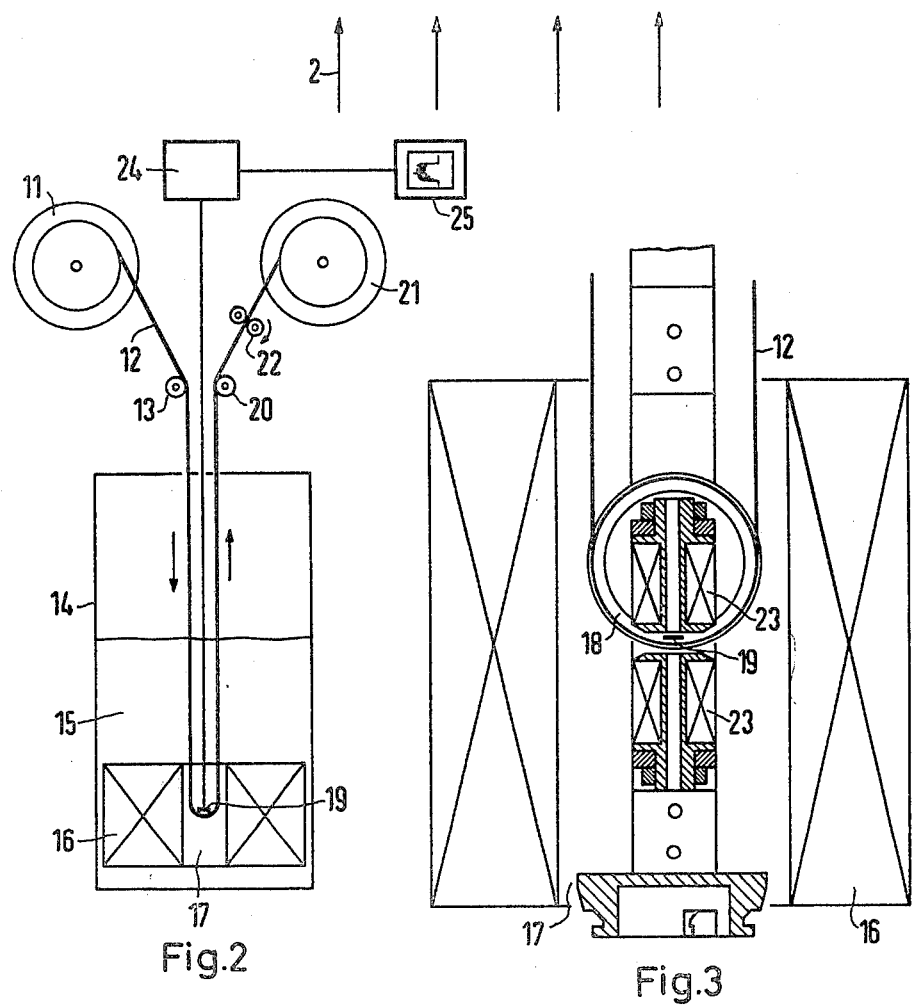
FIG. 2 is a schematic of a preferred apparatus for carrying out the method according to the present invention.

The measured signals of the Hall probe 19 are fed, as shown schematically in FIG. 2, to a compensator 24 having its output connected to chart recorder 25, for instance, for recording the compensated measured signals. Compensator 24 may simply comprise a suitable amplifier with bias to compensate for the initial field strength.

Figure 4:
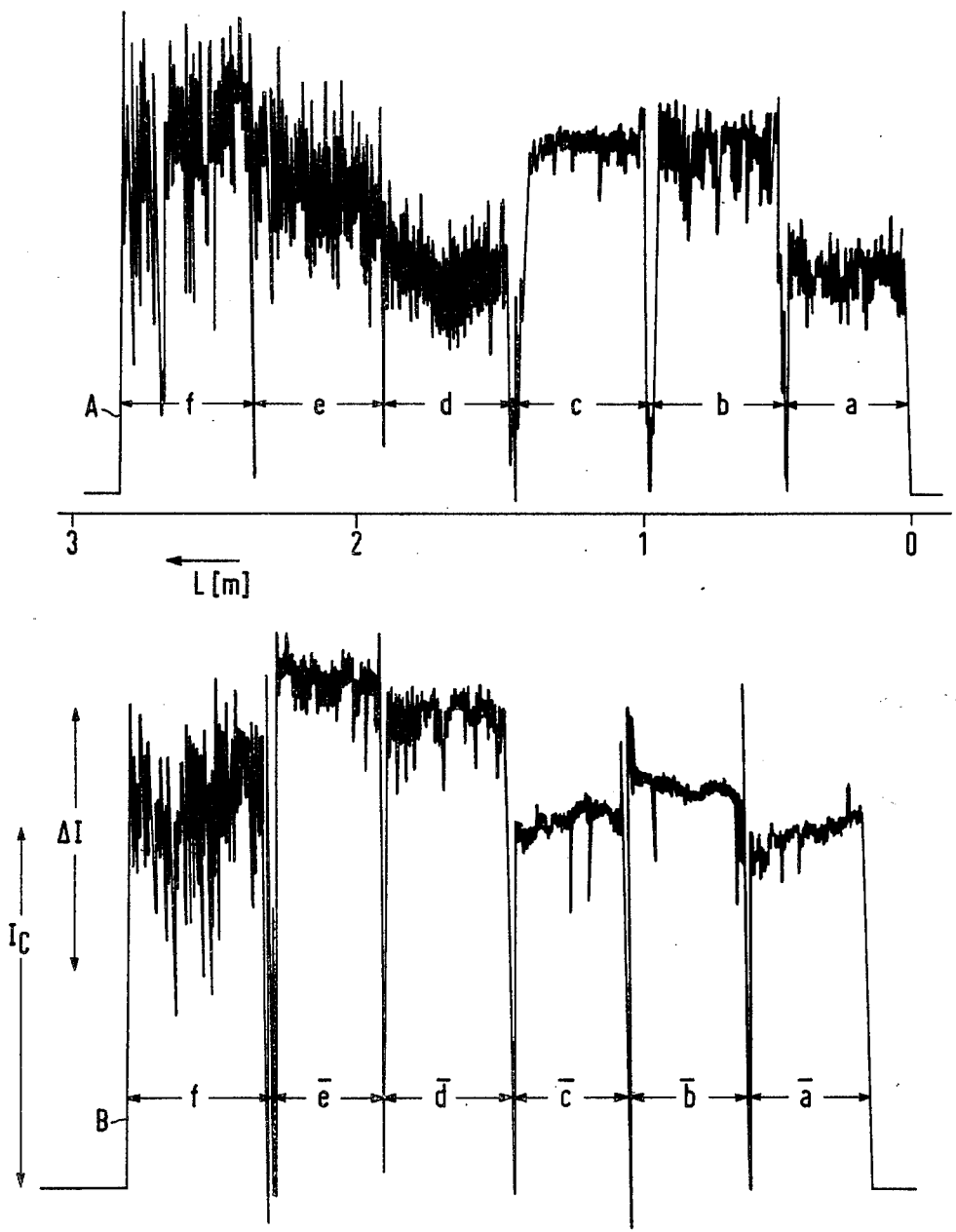
FIG. 4 is a series of wave-forms representing measured values obtained with the method according to the present invention.

Two recordings recorded by means of such a chart recorder are shown on FIG. 4. Since the paper used for recording runs through the recorder from left to right, the diagrams are recorded from the right to the left. The chart recorder traces the measured compensated Hall voltage as a function of the time of the respective measurement on the travelling paper chart. On FIG. 4, the recording time and the compensated Hall voltage have already been converted into other quantities for the purpose of evaluating the diagrams. On the abscissa, the distance L of the respective examined point of the conductor from the beginning of the examined conductor is given. This distance can be determined without difficulty from the recording time and the travel velocity of the conductor. Along the ordinate the critical current of the conductor, for which the compensated Hall voltage is a measure as explained above, is plotted.

The structure of the recorded curves is brought about by a number of effects, which will be discussed in the following with reference to an example using a conductor ribbon with a coating of superconductive $Nb_3Sn$ layer:

First, the surface roughness of the ribbon can cause the distance between the ribbon and the Hall probe to vary. So that these distance changes lead to only a relatively small change of the Hall voltage, it is advisable to make the distance large, although this reduces the sensitivity of the measurement. In an arrangement as shown in FIGS. 2 and 3, a distance change of 0.01 mm leads to a Hall voltage change of about 1.8%.

Microdefects may also be present. These lead to a reduction of the cross section of the superconductor, and inhomogeneities in the composition of the superconducting layer, which lead to variations in the critical current. These variations always appear on the recorder diagram at the same location in repeated runs. Upon variation of the magnetic field they should be independent of the field, relative to the mean value, if they are caused by changes in the cross section. Inhomogeneities, on the other hand, should generate Hall voltage changes which are dependent on the magnetic field, since the critical current of these places exhibits a magnetic field dependence different from that of the homogeneous superconductive material. In general, the Hall voltage variations caused by inhomogeneities will increase with the field since such places usually have low critical fields.

Thermal instabilities due to the high field change rate when passing the ribbon to be examined through the external magnetic field can manifest themselves by flux discontinuities. At the points where the magnetic flux has penetrated partially or completely, the Hall voltage changes. This process should largely be of a statistical nature. In detail, the Hall voltage is reduced more in the event of flux jumps; the later the part of the conductor affected by the flux jump carries the full critical current again. Because of the decreasing magnetization of the superconductive material with increasing external magnetic field, the susceptibility to flux jumps decreases with increasing magnetic field. In addition, the fluctuations of the Hall voltage should become smaller the better the stability of the conductor tested.

From the regularity and the dependence of the Hall voltage fluctuations on the magnetic field, conclusions can therefore be drawn as to their cause. Since the effects of the surface roughness of the conductor can be suppressed to a very large extent by a suitable choice of the distance between the conductor and the Hall probe, there remain essentially the Hall voltage variations caused by microdefects and inhomogeneities as well as those by flux jumps.

The variations by microdefects and inhomogeneities can easily be isolated, since they must always appear at the same point of the conductor when the tested conductor runs through the test equipment repeatedly.

The variations caused by thermal instabilities, on the other hand, can be evaluated only statistically. The critical current $I_c$ is determined by the excursion up to the average on the recorder diagram, as indicated in FIG. 4. The variations of the deflection about the average is designated $\Delta I$ and indicates the instabilities that occur. As a measure of the degree of instability the quotient $\Delta I/I_c$ is used. In a perfectly stable ribbon, $\Delta I = 0$. With increasing instability, $\Delta I/I_c$ also increases.

The measurements explained in the following example show further that the quotient $\Delta I/I_c$ can be considered a suitable measure for the stability or instability of a conductor due to its dependence on different stabilization measures and on the external magnetic field.

In preparation for the measurement, several superconductors which would be expected to have differing stability behavior were fabricated. A ribbon about 70 $\mu m$ thick with a $Nb_3Sn$ coating about 9 $\mu m$ thick at the surface obtained by deposition from the gaseous phase, and a ribbon about 80 $\mu m$ thick with an $Nb_3Sn$ coating about 14 $\mu m$ thick, similarly prepared by deposition from the gaseous phase, were each cut into three pieces about 40 cm long and subsequently electroplated with silver. Both ribbons were about 2 mm wide. One piece of each ribbon was given a silver coating of about 6 μm, another piece, a coating of about 20 μm and a third piece in each case a coating with a thickness of about 40 μm. The individual pieces of ribbon were then soldered together and pulled through the test equipment and measured repeatedly in a constant external magnetic field. The magnetic induction of the magnetic field applied was between 2 and 5 tesla.

The measurement results in a magnetic field of 4 T are shown on Curve A of FIG. 4 as an example of the recorder diagrams obtained with these measurements.

Subsequently, a copper ribbon 50 μm thick was soldered onto the broad sides of all sections of ribbon for the last section of ribbon which had an $Nb_3Sn$ coating 14 μm thick and a silver layer 40 μm thick. Then, the ribbon-shaped conductor was measured again in constant external magnetic fields of 2 to 5 T. The results obtained in a magnetic field of 4 T are shown on Curve B of FIG. 4.

In the diagrams shown in FIG. 4, the diagram parts belonging to the individual sections of ribbon are designated with the letters that can be taken from the following Table:

| Thickness of the $Nb_3Sn$ layer (um) | 9 | | | 14 | | |
|---|---|---|---|---|---|---|
| Thickness of the silver layer (um) | 6 | 20 | 40 | 6 | 20 | 40 |
| without copper ribbons | a | b | c | d | e | f |
| with copper ribbons | ā | b̄ | c̄ | d̄ | ē | |

The diagrams obtained in different external magnetic fields showed patterns similar to the diagrams obtained in an external magnetic field of 4 T.

On Curve A as well as on Curve B of FIG. 4, the almost normally conducting solder joints, by which the sections of ribbon were joined together, can clearly be recognized by the particularly large deflections between the curve sections belonging to the individual sections of ribbon. At these solder joints, which have an effect similar to interruptions of the superconducting layer within a coherent piece of conductor, the critical current is particularly low.

As Curves A and B further show, a critical current $I_c$ which is defined by the recorder deflection up to the average of the recorded curve, can be determined for each section of ribbon. The variations of the deflection about the average are designated Δ I. In some ribbon sections, spike-like deflections occurred reproducibly at the same points of the ribbon after the copper ribbons were soldered on, in different, successive measurements (see, for instance, ribbon section c̄). Such deflections were not included in the determination of Δ I, since they cannot be traced to instabilities but must have been caused either by damage to the $Nb_3Sn$ layer or by inadequate connection between the superconductive layer and the copper ribbon.

As FIG. 4 and also the measurements in external magnetic fields of different magnitudes show, the different stabilization measures have an effect on the critical current $I_c$ as well as also an effect on the degree of stability, i.e., Δ $I/I_c$. $I_c$ increases with the thickness of the silver coating applied and is increased still more by soldering on copper ribbons. The quotient Δ $I/I_c$ decreases with increasing thickness of the silver layer. A further reduction of Δ $I/I_c$, i.e., a further increase of the stability, is obtained by soldering the copper ribbons. Only the ribbon sections c and c̄, whose irregular values were traced, as further investigations showed, to poor contact between the $Nb_3Sn$ layer and the silver layer are not in line with these results. As expected, $I_c$ and Δ $I/I_c$ decrease with increasing external magnetic field, i.e., the critical current becomes smaller while the stability increases. The velocity of the ribbons passing through the test equipment was at first 1 m/min during the measurements which, with a magnetic field of 2 T, corresponds to a field change rate of 64 tesla/min and with a magnetic field of 5 T, to a field change rate of 159 tesla/min. In the measurements described above, changes in the running speed of the ribbons and therefor, of the field change rate by factors of 0.25 to 2.5 had no influence on the measurement results.

Control measurements obtained by measuring the same ribbon several times and comparisons with conventional measurements, using short pieces of ribbon, showed that the measuring method according to the present invention has no adverse effect on the quality of the measured ribbons.

The method according to the present invention is therefore highly suited for measuring the magnitude and the position dependence of the critical current and the stability, particularly in superconductors in ribbon form. In a manner similar to the example described above, the corresponding parameters of multi-core conductors can also be determined continuously without making contact. In multi-core conductors, the transversal currents induced in the normally conducting matrix by the external magnetic field and the influence of the twist of the superconductor cores on these transversal currents can also be determined by means of the method according to the invention, by comparing, for instance, measurements on conductors with different twist lays with each other.

In addition to the examples already explained, the method according to the invention permits a number of further possible variations. The external magnetic field through which the conductor passes can, for instance, be changed monotonically in time while the conductor runs through it, i.e., it can be raised, for instance, gradually from an initially low value to a higher value. This makes it possible to measure, for instance, the dependence of the critical current of the conductor on the external magnetic field by means of a single pass of the conductor. Such a measurement, of course, does not give reliable information regarding the homogeneity of the critical current along the conductor. At the same time, the homogeneity of the critical current and the dependence of the critical current on the external magnetic field can be measured, for instance, by letting the conductor pass successively through magnetic fields of different magnitude and measuring the shielding currents induced in each case via several magnetic field probes. Alternatively, the conductor can be run through a magnetic field which, for instance, increases along the path of the conductor with a number of probes for measuring the respective induced shielding fields arranged along the conductor.

The external magnetic field can furthermore be changed, for instance, periodically in time and the magnetic field produced by the shielding currents can be measured using a phase-sensitive amplifier which is controlled by the temporal change of the external magnetic field. The sensitivity of the measurement method can be increased still further by such a measure through the suppression of noise. In addition induced currents which change with different time constants can be separated from each other. Such currents may be, for instance, the shielding currents in the superconductor material of the conductor, and currents in the normally conducting material, which encounter ohmic resistance, i.e., particularly transversal currents in the matrix of multi-core conductors.

The method according to the present invention can be even used during the fabrication of the conductors to be tested and in particular, between individual steps of the manufacturing process. The measurement data obtained can then be used for controlling or regulating the manufacturing process. These and other modifications may be made without departing from the spirit of the invention which is intended to be limited solely by the appended claims.

What is claimed is:

1. A method for the continuous, contactless testing of a long conductor which consists at least partially of superconductive material comprising moving the conductor, with its superconductive material in the superconducting state, through an external magnetic field which induces shielding currents in the superconductor material, and measuring the magnetic field produced by said shielding currents.

2. The method according to claim 1, wherein the conductor is moved through an external magnetic field which is constant in time.

3. The method according to claim 1, wherein the conductor is moved through an external magnetic field which is variable in time.

4. The method according to claim 1, wherein change in the external magnetic field acting on the conductor is made large enough so that the induced shielding currents in the entire cross section of the superconductor material reach the critical current density.

5. Apparatus for the continuous contactless testing of a long conductor consisting at least partially of superconductive material comprising:
   a. a cryostat;
   b. a cylindrical superconducting magnet coil arranged in the cryostat for generating an external magnetic field;
   c. means for introducing the conductor into the magnetic field of the superconducting magnet coil approximately parallel to the coil axis;
   d. means for deflecting the conductor perpendicular to the coil axis and therefore, to the external magnetic field;
   e. means for bringing the conductor out of said coil approximately parallel to the coil axis; and
   f. at least one magnetic field probe provided in the vicinity of the deflection points of said means for deflection.

6. Apparatus according to claim 5, wherein a magnetic field probe is provided both above and below the conductor in the vicinity of said deflection point.

7. Apparatus according to claim 6, wherein an additional coil is provided at the deflection point for generating an additional, time variable external magnetic field that is directed perpendicular to the conductor.

8. Apparatus according to claim 7, said magnetic field probe is a Hall probe.

9. Apparatus according to claim 5, wherein an additional coil is provided at the deflection point for generating an additional, time-variable external magnetic field that is directed perpendicular to the conductor.

10. Apparatus according to claim 5, said magnetic field probe is a Hall probe.

* * * * *